US010246496B2

(12) United States Patent
Norton et al.

(10) Patent No.: US 10,246,496 B2
(45) Date of Patent: Apr. 2, 2019

(54) POTASSIUM CHANNEL BLOCKERS AND USE THEREOF IN THE TREATMENT OF AUTOIMMUNE DISEASES

(71) Applicants: MONASH UNIVERSITY, Clayton, Victoria (AU); LA TROBE UNIVERSITY, Bundoora, Victoria (AU); PEPTIDES INTERNATIONAL, INC., Louisville, KY (US); BAYLOR COLLEGE OF MEDICINE, Houston, TX (US)

(72) Inventors: Raymond S. Norton, Rosanna (AU); Shih Chieh Chang, Singapore (SG); Michael W. Pennington, Shelbyville, KY (US); Christine Beeton, Pearland, TX (US); Brian J. Smith, Sunbury (AU)

(73) Assignees: LA TROBE UNIVERSITY (AU); MONASH UNIVERSITY (AU); BAYLOR COLLEGE OF MEDICINE, Houston, TX (US); PEPTIDES INTERNATIONAL, INC., Louisville, KY (US)

( * ) Notice: Subject to any disclaimer, the term of this patent is extended or adjusted under 35 U.S.C. 154(b) by 0 days.

(21) Appl. No.: 15/503,841

(22) PCT Filed: Aug. 14, 2015

(86) PCT No.: PCT/AU2015/000487
§ 371 (c)(1),
(2) Date: Feb. 14, 2017

(87) PCT Pub. No.: WO2016/023072
PCT Pub. Date: Feb. 18, 2016

(65) Prior Publication Data
US 2017/0362286 A1 Dec. 21, 2017

(30) Foreign Application Priority Data

Aug. 15, 2014 (AU) ................................ 2014903189

(51) Int. Cl.
A61K 38/00 (2006.01)
A61K 38/17 (2006.01)
C07K 14/435 (2006.01)
C12N 15/63 (2006.01)
C07K 4/00 (2006.01)
C07K 19/00 (2006.01)

(52) U.S. Cl.
CPC ........ C07K 14/43595 (2013.01); A61K 38/17 (2013.01); C07K 14/43504 (2013.01); C12N 15/63 (2013.01); A61K 38/00 (2013.01); C07K 4/00 (2013.01); C07K 19/00 (2013.01); C07K 2319/21 (2013.01)

(58) Field of Classification Search
None
See application file for complete search history.

(56) References Cited

U.S. PATENT DOCUMENTS 7,820,623 B2   10/2010   Sullivan et al.
8,734,796 B2 *  5/2014   Walker ............. A61K 39/39591
                                                424/134.1

FOREIGN PATENT DOCUMENTS

WO    WO 2006-042151 A2    4/2006
WO    WO 2010-108154 A2    9/2010

OTHER PUBLICATIONS

Yamaguchi et al., "Screening and cDNA Cloning of Kv1 Potassium Channel Toxins in Sea Anemones," Mar. Drugs 2010, 8, 2893-2905 (Year: 2010).*
Pennington et al. "Engineering a Stable and Selective Peptide Blocker of the Kv1.3 Channel in T Lymphocytes," Molecular Pharmacology, 2009, vol. 75, No. 4, pp. 762-773 (Year: 2009).*
Fonesca et al. "Recent advances in the use of cell-penetrating peptides for medical and biological application," Advanced Drug Delivery Reviews 61 (2009) 953-964 (Year: 2009).*
Kim et al. "The N-Terminal Methionine of Cellular Proteins as a Degradation Signal," Cell 156, 158-169, Jan. 16, 2014 (Year: 2014).*
Beeton et al. "Targeting effector memory T cells with a selective peptide inhibitor of Kv1.3 channels for therapy of autoimmune diseases," Molecular Pharmacology, Apr. 2005, vol. 67, No. 4, pp. 1369-1381.
Kalman et al. ShK-Dap22, a Potent Kv1.3-specific Immunosuppressive Polypeptide, Journal of Biological Chemistry, Dec. 1998, vol. 273, No. 49, pp. 32697-32707.
Pennington et al. "Engineering a Stable and Selective Peptide Blocker of the Kv1.3 Channel in T Lymphocytes," Molecular Pharmacology, Apr. 2009, vol. 75, No. 4, pp. 762-773.

(Continued)

Primary Examiner — Christina Bradley
(74) Attorney, Agent, or Firm — Sheridan Ross P.C.

(57) ABSTRACT

Novel analogues of the sea anemone *Stichodactyla helianthus* toxin ShK, and their use as, for example, therapeutic agents for treating autoimmune diseases are disclosed. The analogues comprise a ShK toxin polypeptide and an N-terminal extension comprising an amino acid sequence according to formula (I): wherein $X^{-4}$ is D, E or other negatively-charged amino acid or derivative thereof, $X^{-3}$ is E, I, L, S, V, W or a tryptophan derivative, $X^{-2}$ is any amino acid, $X^{-1}$ is any amino acid, a is absent or a first additional moiety, and b is absent or a second additional moiety.

$a\text{-}X^{-4}X^{-3}X^{-2}X^{-1}\text{-}b(\text{SEQ ID NO: 3})$    (I)

15 Claims, 3 Drawing Sheets
Specification includes a Sequence Listing.

(56) References Cited

OTHER PUBLICATIONS

Shen et al. "Probing water micro-solvation in proteins by water catalysed proton-transfer tautomerism," Nature Communications, Nov. 2013, vol. 4, 2611, 7 pages.
Extended Search Report for European Patent Application No. 15832619.9, dated Dec. 14, 2017, 12 pages.
International Search Report and Written Opinion prepared by the Korean Intellectual Property Office dated Oct. 19, 2015, for International Application No. PCT/AU2015/000487.
Pennington et al., "A C-terminally amidated analogue of ShK is a potent and selective blocker of the voltage-gated potassium channel Kv1.3" FEBS Letters, vol. 586, No. 22, pp. 3996-4001 (2012).
Rashid et al., A potent and selective peptide blocker of the Kv1.3 channel: prediction from free-energy simulations and experimental confirmation: PLoS One, vol. 8, Issue 11, Article No. e78712, Internal pp. 1-10 (2013).
Chi et al., "Development of a sea anemone toxin as an immunomodulator for therapy of autoimmune diseases" Toxicon. Mar. 15, 2012; 59(4): 529-546.

\* cited by examiner

```
Kv1.1  ****** ELGLLIFFLFIGVILFSSAVYFAEAEEAESHFSSIPDAFWWAVVSMTTVGYGDMYPVTIGGKIVGSLCAIAGVLTIALPVPVIVSNFNYFY  SEQ ID NO: 11
Kv1.3  ****** ELGLLIFFLFIGVILFSSAAYFAEADDPSSGFNSIPDAFWWAVVTMTTVGYGDMHPVTIGGKIVGSLCAIAGVLTIALPVPVIVSNFNYFY  SEQ ID NO: 12
```

*Figure 2*

SEQUENCE LISTING

<160> NUMBER OF SEQ ID NOS: 18

<210> SEQ ID NO 1
<211> LENGTH: 4
<212> TYPE: PRT
<213> ORGANISM: Artificial Sequence
<220> FEATURE:
<223> OTHER INFORMATION: N-terminal extension modification of ShK

<400> SEQUENCE: 1

Glu Ser Ser Ser
1

<210> SEQ ID NO 2
<211> LENGTH: 4
<212> TYPE: PRT
<213> ORGANISM: Artificial Sequence
<220> FEATURE:
<223> OTHER INFORMATION: N-terminal extension modification of ShK

<400> SEQUENCE: 2

Glu Trp Ser Ser
1

<210> SEQ ID NO 3
<211> LENGTH: 4
<212> TYPE: PRT
<213> ORGANISM: Artificial Sequence
<220> FEATURE:
<223> OTHER INFORMATION: N-terminal extension modification of ShK
<220> FEATURE:
<221> NAME/KEY: misc_feature
<222> LOCATION: (1)..(1)
<223> OTHER INFORMATION: Xaa is D, E or other negatively-charged amino
      acid or derivative thereof
<220> FEATURE:
<221> NAME/KEY: misc_feature
<222> LOCATION: (2)..(2)
<223> OTHER INFORMATION: Xaa is E, I, L, S, V, W or a tryptophan
      derivative
<220> FEATURE:
<221> NAME/KEY: misc_feature
<222> LOCATION: (3)..(3)
<223> OTHER INFORMATION: Xaa is any amino acid
<220> FEATURE:
<221> NAME/KEY: misc_feature
<222> LOCATION: (4)..(4)
<223> OTHER INFORMATION: Xaa is any amino acid

<400> SEQUENCE: 3

Xaa Xaa Xaa Xaa
1

<210> SEQ ID NO 4
<211> LENGTH: 35

```
<212> TYPE: PRT
<213> ORGANISM: Stichodactyla helianthus

<400> SEQUENCE: 4

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 5
<211> LENGTH: 4
<212> TYPE: PRT
<213> ORGANISM: Artificial Sequence
<220> FEATURE:
<223> OTHER INFORMATION: N-terminal extension modification of ShK

<400> SEQUENCE: 5

Glu Glu Ser Ser
1

<210> SEQ ID NO 6
<211> LENGTH: 4
<212> TYPE: PRT
<213> ORGANISM: Artificial Sequence
<220> FEATURE:
<223> OTHER INFORMATION: N-terminal extension modification of ShK

<400> SEQUENCE: 6

Glu Trp Ser Thr
1

<210> SEQ ID NO 7
<211> LENGTH: 4
<212> TYPE: PRT
<213> ORGANISM: Artificial Sequence
<220> FEATURE:
<223> OTHER INFORMATION: N-terminal extension modification of ShK

<400> SEQUENCE: 7

Glu Trp Thr Thr
1

<210> SEQ ID NO 8
<211> LENGTH: 4
<212> TYPE: PRT
<213> ORGANISM: Artificial Sequence
<220> FEATURE:
<223> OTHER INFORMATION: N-terminal extension modification of ShK

<400> SEQUENCE: 8

Glu Trp Thr Ser
1

<210> SEQ ID NO 9
<211> LENGTH: 5
<212> TYPE: PRT
<213> ORGANISM: Artificial Sequence
<220> FEATURE:
<223> OTHER INFORMATION: N-terminal extension modification of ShK

<400> SEQUENCE: 9

Ser Glu Trp Ser Ser
1               5
```

<210> SEQ ID NO 10
<211> LENGTH: 39
<212> TYPE: PRT
<213> ORGANISM: Artificial Sequence
<220> FEATURE:
<223> OTHER INFORMATION: Stichodactyla helianthus toxin ShK with an
      N-terminal extension modification

<400> SEQUENCE: 10

Glu Trp Ser Ser Arg Ser Cys Ile Asp Thr Ile Pro Lys Ser Arg Cys
1               5                   10                  15

Thr Ala Phe Gln Cys Lys His Ser Met Lys Tyr Arg Leu Ser Phe Cys
            20                  25                  30

Arg Lys Thr Cys Gly Thr Cys
            35

<210> SEQ ID NO 11
<211> LENGTH: 35
<212> TYPE: PRT
<213> ORGANISM: Stichodactyla helianthus

<400> SEQUENCE: 11

Arg Ser Cys Ile Asp Thr Lys Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 12
<211> LENGTH: 35
<212> TYPE: PRT
<213> ORGANISM: Stichodactyla helianthus

<400> SEQUENCE: 12

Arg Ser Cys Ile Asp Thr Ile Pro Lys Ala Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 13
<211> LENGTH: 35
<212> TYPE: PRT
<213> ORGANISM: Stichodactyla helianthus

<400> SEQUENCE: 13

Arg Ser Cys Ile Asp Thr Ile Pro Lys Ser Arg Cys Thr Ala Phe Lys
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 14
<211> LENGTH: 35
<212> TYPE: PRT
<213> ORGANISM: Stichodactyla helianthus

<400> SEQUENCE: 14

```
Arg Ser Cys Ile Asp Thr Ile Pro Lys Ser Arg Cys Thr Ala Phe Gln
1               5                   10                  15

Cys Lys His Lys Met Lys Tyr Arg Leu Ser Phe Cys Lys Thr Cys
            20                  25                  30

Gly Thr Cys
        35

<210> SEQ ID NO 15
<211> LENGTH: 35
<212> TYPE: PRT
<213> ORGANISM: Stichodactyla helianthus

<400> SEQUENCE: 15

Arg Ser Cys Ile Asp Thr Ile Pro Lys Ser Arg Cys Thr Ala Phe Gln
1               5                   10                  15

Cys Lys His Arg Met Lys Tyr Arg Leu Ser Phe Cys Arg Lys Thr Cys
            20                  25                  30

Gly Thr Cys
        35

<210> SEQ ID NO 16
<211> LENGTH: 35
<212> TYPE: PRT
<213> ORGANISM: Stichodactyla helianthus

<400> SEQUENCE: 16

Arg Ser Cys Ile Asp Thr Ile Pro Lys Ser Arg Cys Thr Ala Phe Gln
1               5                   10                  15

Cys Lys His Ser Met Ala Tyr Arg Leu Ser Phe Cys Arg Lys Thr Cys
            20                  25                  30

Gly Thr Cys
        35

<210> SEQ ID NO 17
<211> LENGTH: 35
<212> TYPE: PRT
<213> ORGANISM: Stichodactyla helianthus

<400> SEQUENCE: 17

Arg Ser Cys Ile Asp Thr Ile Pro Lys Ser Arg Cys Thr Ala Phe Gln
1               5                   10                  15

Cys Lys His Ser Met Lys Ala Arg Leu Ser Phe Cys Arg Lys Thr Cys
            20                  25                  30

Gly Thr Cys
        35

<210> SEQ ID NO 18
<211> LENGTH: 35
<212> TYPE: PRT
<213> ORGANISM: Stichodactyla helianthus

<400> SEQUENCE: 18

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Lys Lys Thr Cys
            20                  25                  30

Gly Thr Cys
        35
```

POTASSIUM CHANNEL BLOCKERS AND USE THEREOF IN THE TREATMENT OF AUTOIMMUNE DISEASES

TECHNICAL FIELD

The present invention relates to novel analogues of the sea anemone peptide *Stichodactyla helianthus* toxin ShK, and their use as, for example, therapeutic agents for treating autoimmune diseases.

CROSS REFERENCE TO RELATED APPLICATIONS

This application is a national stage application under 35 U.S.C. 371 and claims the benefit of PCT Application No. PCT/AU2015/000487 having an international filing date of 14 Aug. 2015, which designated the United States, and claims the benefit of Australian Provisional Patent Application No 2014903189 titled "Novel potassium channel blockers" filed on 15 Aug. 2014, the content of which is hereby incorporated by reference in its entirety.

INCORPORATION BY REFERENCE

The following patent specification is referred to in the following description:
International patent specification no WO 2010/108154 titled "Selective and potent peptide inhibitors of Kv1.3". The content of this patent specification is hereby incorporated by reference in its entirety.

REFERENCE TO SEQUENCE LISTING

This application contains a Sequence Listing submitted as an electronic text file named "Sequence_Listing_ST25.txt", having a size in bytes of 6 kb, and created on Jul. 31, 2017. The information contained in the electronic file is hereby incorporated by reference in its entirety pursuant to 37 CFR § 1.52(e)(5).

BACKGROUND

Nearly 70 different autoimmune diseases are known, affecting millions of people worldwide. They involve various organs in the body, such as the joints (eg rheumatoid arthritis; RA), heart, lungs (eg asthma), central nervous system (CNS) (eg multiple sclerosis; MS), endocrine organs (eg type-1 diabetes mellitus; T1DM) and skin (eg psoriasis). Typically, they are characterised by tissue destruction caused by, at least in part, self-reactive T lymphocytes (T cells). As T cells undergo repeated antigen stimulation they differentiate into terminally-differentiated effector memory T ($T_{EM}$) cells (Sallusto F et al., 2000), which are characterised by high expression of the voltage-gated potassium channel Kv1.3 (after activation) and the absence of both the chemokine receptor CCR7 and phosphatase CD45RA on their surfaces (Wulff H et al., 2003). In the autoimmune diseases mentioned above, the disease-associated T cells in patients with RA (synovial T cells), MS (specific for myelin antigens), T1DM (specific for GAD65 antigens), asthma (induced-sputum T cells) and psoriasis, are all $T_{EM}$ cells (Wulff H et al., 2003; Beeton C et al., 2006; Fasth A et al., 2004; Friedrich M et al., 2000; Koshy S et al., 2014; Lovett-Racke A et al et al., 2003; and Viglietta V et al., 2002). In addition, B cells differentiate into class-switched B cells upon recurring antigen stimulation and are also implicated in MS (Corcione A et al., 2004) and other autoimmune diseases; these cells are a major source of IgG autoantibodies that result in direct tissue damage in RA, MS and T1DM (Berger T et al., 2003; O'Connor K C et al., 2001; Atkinson M A et al., 2001; and Domer T et al., 2003). Similarly to $T_{EM}$ cells, class-switched B cells up-regulate the Kv1.3 potassium channel upon activation and their proliferation can be suppressed through the inhibition of Kv1.3 (Wulff H et al., 2003; and Wulff H et al., 2004). On the other hand, CCR7⁺ naïve and central memory ($T_{CM}$) cells are less sensitive to the inhibition of Kv1.3 as they up-regulate KCa3.1 channels upon activation (Wulff H et al., 2003), as do naïve and IgD⁺CD27⁺ memory B cells, which are also insensitive to Kv1.3 blocking agents (Wulff H et al., 2003). As a consequence, selective blocking agents of Kv1.3 are expected to reduce the severity of autoimmune diseases without inducing generalised immunosuppression (Beeton C et al., 2011; and Chi V et al., 2012). Recently, it has also been shown that blocking the Kv1.3 channels has additional therapeutic potential. For example, blocking Kv1.3 with peptides such as ShK, scorpion toxin margatoxin (MgTX) and charybdotoxin (ChTX), prevents the proliferation of CD8⁺ cytotoxic effector memory T cells and their secretion of granzyme B (GrB), which is toxic to the neuronal cells (Hu L N et al., 2013). These findings indicate that Kv1.3 is not only an attractive therapeutic target for immunomodulation but also plays an important role in neuron protection.

One of the most potent inhibitors of Kv1.3 channels is the sea anemone peptide ShK, which blocks Kv1.3 with an $IC_{50}$ of 11 pM (Kalman K et al., 1998). ShK is a 35-residue polypeptide consisting of two short α-helices comprising amino acids 14-19 and 21-24 stabilised by three disulphide bridges (Tudor J E et al., 1996). ShK interacts with all four subunits of the Kv1.3 channel tetramer, with Lys22 occluding the channel pore (Kalman K et al., 1998). ShK has been shown to suppress proliferation of $T_{EM}$ cells and improve the condition of two animal models of MS (ie chronic relapse-remitting experimental autoimmune encephalomyelitis (CR-EAE) and adoptive transfer of experimental autoimmune encephalomyelitis (at-EAE) (Beeton C et al., 2006)), the pristane-induced arthritis (PIA) model of RA, and animal models of asthma and psoriasis (Koshy S et al., 2014; and Gilhar A et al., 2011). However, while ShK has considerable therapeutic potential, unfortunately it also binds to the closely-related Kv1 channel subtype, Kv1.1 (Kd=16 pM) that is found in the CNS and heart (Gutman G A et al., 2005). Since it has been shown that Kv1.1-deficient mice exhibit cardiac dysfunction associated with epileptic activity (Glasscock E et al., 2010), there is a need for Kv1.3-selective analogues to be developed in order to avoid potential cardiac- and neuro-toxicity, especially in subjects with MS whose blood-brain barrier (BBB) is disrupted or compromised such that exogenous peptides and proteins may gain entry into the CNS (Bennett J et al., 2010).

Several analogues of ShK with enhanced Kv1.3-selectivity have been synthesised. However, many of these previous analogues included amino acid substitutions with unnatural (ie non-canonical) amino acids and/or non-protein extensions to their N-terminal (Kalman K et al., 1998; Beeton C et al., 2003; and Pennington M W et al., 2009). One such analogue of ShK, known as ShK-186, has recently entered clinical trials for the treatment of a range of autoimmune diseases. This analogue contains an N-terminal phosphotyrosine (pTyr) and a C-terminal amide; the latter was introduced to avoid carboxypeptidase degradation and has no effect on binding affinity (Tarcha E J et al., 2012). ShK-186 is, however, not wholly satisfactory since it is rapidly dephosphorylated in vivo (Tarcha E J et al., 2012) and, further, induces low titre anti-ShK-186 antibody production (Beeton C et al., 2003). Another ShK analogue, known as ShK-192, differs from ShK-186 by the substitution of a methionine (Met21) with norleucine (Nle) to reduce the potential for oxidative metabolism, and the replacement of the phospho moiety with a non-hydrolysable phosphono group. It has been found that while ShK-192 has a slightly lower binding affinity for Kv1.3 channels, it shows a significantly improved level of selectivity over Kv1.1; it is predicted to bind to the extracellular face of the channel with the terminal negatively-charged phosphono group forming a salt bridge with the side-chain ammonium group of Lys411 in Kv1.3 (Pennington M W et al., 2009).

In work leading to the present invention, the applicants employed computational techniques to investigate potential modifications to the ShK toxin to improve selectivity for Kv1.3 channels over Kv1.1 channels. The modifications that were investigated included an N-terminal extension of ShK with the tetrapeptide sequence ESSS (SEQ ID NO: 1) based upon a hypothesis that this extension could mimic the phosphono moiety of the ShK-192 analogue. Molecular dynamics (MD) simulations subsequently indicated that a tryptophan (Trp) at position −3 of the tetrapeptide would be favourable in forming a stable interaction with Pro377 of Kv1.3, so an ShK analogue including an N-terminal extension of EWSS (SEQ ID NO: 2) was also investigated. ShK analogues with novel N-terminal tetrapeptide extensions were therefore designed and produced; electrophysiology results showed that the analogue [EWSS]ShK retains potency against Kv1.3 with an $IC_{50}$ of 34 pM, but shows a markedly higher level of selectivity for Kv1.3 channels over Kv1.1 channels. These results indicate that the [EWSS]ShK analogue and related analogues may be suitable for use as, for example, therapeutic agents for treating autoimmune disease.

SUMMARY

Thus, in a first aspect, the present invention provides an analogue of *Stichodactyla helianthus* toxin ShK comprising an ShK toxin polypeptide and an N-terminal extension comprising an amino acid sequence according to formula (I):

$$a\text{-}X^{-4}X^{-3}X^{-2}X^{-1}\text{-}b \text{ (SEQ ID NO: 3), wherein} \quad (I)$$

$X^{-4}$ is D, E or other negatively-charged amino acid or derivative thereof,
$X^{-3}$ is E, I, L, S, V, W or a tryptophan derivative,
$X^{-2}$ is any amino acid,
$X^{-1}$ is any amino acid,
a is absent or a first additional moiety, and
b is absent or a second additional moiety.

Accordingly, the ShK analogue may be according to formula (II):

$$a\text{-}X^{-4}X^{-3}X^{-2}X^{-1}\text{-}b\text{-[ShK toxin polypeptide]} \quad (II)$$

Preferably, $X^{-4}$ is E, $X^{-3}$ is W, and $X^{-2}$ and $X^{-1}$ are independently selected from S and T.

In a second aspect, the present invention provides a method of inhibiting T lymphocyte or class-switched B cell proliferation in a subject, said method comprising administering to the subject an effective amount of the analogue of the first aspect, optionally in combination with a pharmaceutically acceptable carrier.

Further, in a third aspect, the present invention provides a method of treating an autoimmune disease in a subject, said method comprising administering to the subject an effective amount of the analogue of the first aspect, optionally in combination with a pharmaceutically acceptable carrier.

In a fourth aspect, the present invention provides the use of the analogue of the first aspect in the treatment of an autoimmune disease, preferably an autoimmune disease mediated by $T_{EM}$ cells such RA and MS.

Moreover, in a fifth aspect, the present invention provides the use of the analogue of the first aspect in the preparation of a medicament for treating an autoimmune disease, preferably an autoimmune disease mediated by $T_{EM}$ cells such as RA and MS.

BRIEF DESCRIPTION OF FIGURES

FIG. 2 provides a sequence alignment of the respective transmembrane regions of the Kv1.1 and Kv1.3 potassium channels: Annotation highlights sequence conservation between two sequences (asterisks=conserved); surface-exposed residues that differ between the two sequences are highlighted in grey, residues in the selectivity filter are boxed and helices are underlined.

DETAILED DESCRIPTION

Figure 1:
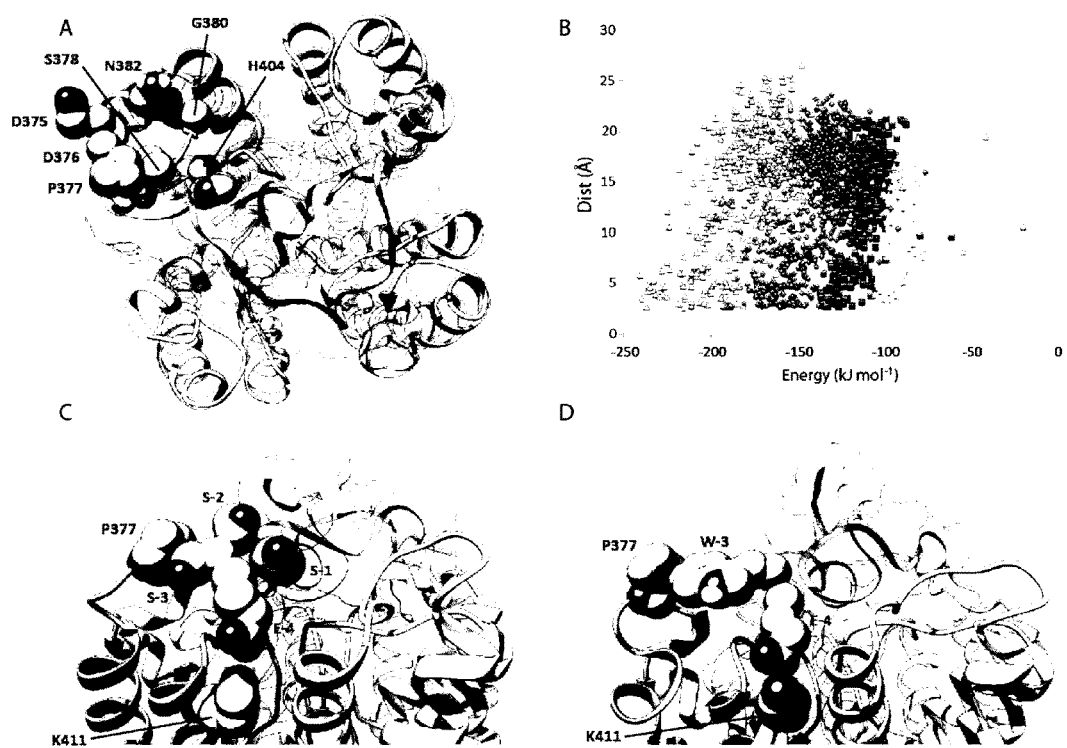
FIG. 1 depicts homology modelling of ShK analogues in complex with Kv1.3: (A) Shows ShK-192 in complex with Kv1.3 as viewed perpendicularly to the membrane plane with the channel represented as a ribbon and the ShK analogue as a transparent surface. The side chain atoms of the amino acids on the surface of the channel that differ between Kv1.1 and Kv1.3 are illustrated as spheres; (B) Shows a comparison of MODELLER energies and separation between the N-terminal Glu of the ShK analogue and Lys411 of the channel. Extensions to ShK of 1 (dark triangle, E), 2 (square, ES), 3 (diamond, ESS) and 4 (pale triangle, ESSS) amino acid residues; (C) Shows a homology model of an analogue according to the present invention, namely [ESSS]ShK, in complex with Kv1.3. The side-chain atoms of Pro377 and Lys411 of the channel are represented as spheres. The side-chain atoms of the 4-amino acid residue extension, ESSS (SEQ ID NO: 1), are represented as spheres; and (D) Shows a homology model of a further analogue according to the present invention, in this case [EWSS]ShK, in complex with Kv1.3. The side-chain atoms of Pro377 and Lys411 of the channel are highlighted. The side-chain atoms of the first two residues (EW) of the 4-amino acid residue extension, EWSS (SEQ ID NO: 2), are represented as spheres.

The amino acid sequence of native or "wild-type" (WT) ShK polypeptide is as follows:

(SEQ ID NO: 4)
RSCIDTIPKSRCTAFQCKHSMKYRLSFCRKTCGTC.

The structure of the ShK polypeptide consists of two short α-helices comprising amino acids 14-19 and 21-24 stabilised by three disulphide bridges between Cys3-Cys35, Cys12-Cys28 and Cys17-Cys32 (Tudor J E et al., 1996). ShK blocks Kv1.3 potassium channels by binding to all four subunits through its interaction with a shallow "vestibule" at the outer entrance of the ion conduction pathway (Lanigan M D et al., 2002). It is believed that at this position, the Lys22 residue of the ShK polypeptide occludes the channel pore like a "cork in a bottle" (Kalman K et al., 1998; Lanigan M D et al., 2002).

ShK analogues with novel N-terminal tetrapeptide extensions were designed and produced either recombinantly or by chemical synthesis. It was found that these analogues retain ShK activity (ie in being capable of blocking Kv1.3), but can also possess a markedly higher level of selectivity for Kv1.3 channels (ie over Kv1.1 channels). As such, the ShK analogues offer significant potential as therapeutic agents for the treatment of autoimmune diseases while avoiding generalised immunosuppression and possible cardiac- and neuro-toxicity through inhibition of off-target channels, particularly Kv1.1.

Thus, in a first aspect, the present invention provides an analogue of *Stichodactyla helianthus*toxin ShK comprising an ShK toxin polypeptide and an N-terminal extension comprising an amino acid sequence according to formula (I):

$$a\text{-}X^{-4}X^{-3}X^{-2}X^{-1}\text{-}b \text{ (SEQ ID NO: 3), wherein} \quad (I)$$

$X^{-4}$ is D, E or other negatively-charged amino acid or derivative thereof,
$X^{-3}$ is E, I, L, S, V, W or a tryptophan derivative,
$X^{-2}$ is any amino acid,
$X^{-1}$ is any amino acid,
a is absent or a first additional moiety, and
b is absent or a second additional moiety.

Accordingly, the ShK analogue may be according to formula (II):

$$a\text{-}X^{-4}X^{-3}X^{-2}X^{-1}\text{-}b\text{-}[\text{ShK toxin polypeptide}] \quad (II)$$

The ShK toxin polypeptide may comprise an amino acid sequence corresponding to that shown above as SEQ ID NO: 4. However, it will be understood by those skilled in the art that the ShK toxin polypeptide may also be a polypeptide that comprises a variant amino acid sequence of SEQ ID NO: 4 that may include one or more minor sequence variations which, preferably, do not substantially alter the function of the peptide (eg despite the variation(s), the peptide maintains the ability of binding to and blocking the activation the potassium channel Kv1.3). Such variation(s) may include one or more conservative amino acid substitutions such as: G, A, V, I, L, M; D, E; N, Q; S, T; K, R, H; F Y, W, H; and P, Nα-alkylamino acids. Other substitutions may include the substitution of one or more L-amino acid(s) with a D-amino acid(s). Preferably, any amino acid substitution comprises a substitution with an amino acid selected from the twenty (20) standard amino acids encoded by the genetic code (ie the canonical amino acids). However, amino acid substitutions with non-canonical amino acids such as, for example, certain Nα-alkylamino acids (eg N-methyl glycine (sarcosine) and N-methyl alanine), and other amino acids such as 2-aminobutyric acid (Abu), naphthylalanine (Nal), amino isobutyric acid, 3-aminoadipic acid (Aad), ornithine, citruline, amino-oxyserine, homo-arginine, nor-leucine (Nle), aminosuberic acid and β-2- and β-3-napthyl-alanine, ring-substituted phenylalanine (Phe) derivatives (eg 2,3,4,5,6-pentafluoro-phenylalanine, 4-chloro-phenylalanine, methyl-phenylalanine and phosphono-phenylalanine), phospho-tyrosine (pTyr), selenocysteine and selenomethionine, are also contemplated. Other sequence variations that may be present include one or more amino acid deletion or addition (eg insertion). Other additions that may be made to, for example, the C-terminal sequence may comprise the addition of a single amino acid (eg Ala), short amino acid sequences (eg 2 to 10 amino acids in length) or long amino acid sequences (eg 11 or more amino acids) which may confer various additional functionalities or properties, such as improved bioavailability, protein recovery or expression (eg a fusion partner); although, typically, a polypeptide provided with an additional amino acid sequence will have a total length of not more than about 75 amino acids, more preferably not more than about 50 amino acids. One preferred example of an addition that may be made to the C-terminal sequence is the addition of a cell-penetrating peptide (CPP). CPPs are short peptides that can facilitate cellular uptake of a molecular cargo such as a peptide or polypeptide. Accordingly, use of a CPP with a ShK analogue of the present invention can enable delivery of the ShK analogue to the cytoplasm of a cell where it may act to block Kv1.3 channels of the mitochondria (mitoKv1.3). Mitochondrial Kv1.3 channels have been shown to be directly involved in cell death by serving as a target of pro-apoptotic Bax and Bak proteins (which inhibit mitoKv1.3 by directly binding into the pore of the channel to inhibit the channel in a "toxin-like mechanism"; Leanza L et al., 2015). As such, compounds that inhibit mitochondrial Kv1.3 channels (eg clofazimine; Leanza L et al., 2013), such as the ShK analogues of the present invention, may be suitable for use as therapeutic agents for treating cancers and other proliferative diseases and disorders. CPPs suitable for use with the ShK analogues of the present invention are well known to those skilled in the art, including for example, the HIV-1 Tat-derived CPP (amino acids 48-60; Wagstaff K M and D A Jans, 2006) and the 9 amino acid transduction domain fragment thereof (Ruben S et al., 1989; and Fawell S et al., 1994), the HIV-1 Rev protein-derived CPP (amino acids 34-50), and the *Drosophila* Antennapedia-derived CPP (amino acids 43-58).

A specific ShK variant polypeptide that may be used in the analogue of the present invention is one that includes a substitution of the Met21 residue with Nle. This substitution is found in the ShK analogue, ShK-192. Alternatively, Met21 may be substituted with, for example, any one of Ala, Val, Ile and Leu. Such substitutions may confer a stabilising effect to oxidation at this position of the ShK polypeptide.

Other specific ShK variant polypeptides that may be used in the analogue of the present invention are described in International patent specification no WO 2010/108154, the entire content of which is hereby incorporated herein by reference. Among those described are ShK polypeptides that include: a substitution of Ser2 with Glu; a substitution of Ile4 with Lys, Glu or Ala; a substitution of Ser10 with Arg or Glu; a substitution of Phe15 with Ala; a substitution of Lys30 with Arg or Glu; a substitution of Thr31 with Nal; and a substitution of Thr34 with Nal. All of these substitutions were found to improve the ShK polypeptide inhibition of Kv1.3 (ie relative to the WT ShK polypeptide). Other ShK polypeptides including the following amino acid substitutions were found to show improved selectivity to Kv1.3 without substantial change to Kv1.3 inhibitory activity (ie relative to the WT ShK polypeptide): substitution of Ile7 with Lys; substitution of Ser10 with Ala; substitution of Gln16 with Lys or Nal; substitution of Ser20 with Lys or Arg; substitution of Lys22 with Ala; substitution of Tyr23 with Ala; substitution of Ser26 with Nal; substitution of Phe27 with Nal; and substitution of Arg29 with Lys or Nal. Accordingly, ShK variant polypeptides that may be used in the analogue of the present invention may be selected from, for example, polypeptides consisting of one of the following amino acid sequences:

```
                                          (SEQ ID NO: 11)
RSCIDTKPKSRCTAFQCKHSMKYRLSFCRKTCGTC (SEQ ID NO: 12)
RSCIDTIPKARCTAFQCKHSMKYRLSFCRKTCGTC (SEQ ID NO: 13)
RSCIDTIPKSRCTAFKCKHSMKYRLSFCRKTCGTC (SEQ ID NO: 14)
RSCIDTIPKSRCTAFQCKHKMKYRLSFCRKTCGTC (SEQ ID NO: 15)
RSCIDTIPKSRCTAFQCKHRMKYRLSFCRKTCGTC (SEQ ID NO: 16)
RSCIDTIPKSRCTAFQCKHSMAYRLSFCRKTCGTC (SEQ ID NO: 17)
RSCIDTIPKSRCTAFQCKHSMKARLSFCRKTCGTC (SEQ ID NO: 18)
RSCIDTIPKSRCTAFQCKHSMKYRLSFCKKTCGTC
```

$X^{-4}$ is D, E or other negatively-charged amino acid or derivative thereof (eg a glutamic acid derivative such as γ-carboxyglutamate, and 2-aminohexanedioic acid (also known as 2-aminoadipic acid)) capable of forming a salt bridge with the side-chain ammonium group of Lys411 of the Kv1.3 channel.

In some preferred embodiments of the amino acid sequence of formula (I), $X^{-4}$ is E.

$X^{-3}$ is E, I, L, S, V, W or a tryptophan derivative (eg a fluorescent azatryptophan), but more preferably is selected from E, S, W or a tryptophan derivative.

In some preferred embodiments of the amino acid sequence of formula (I), $X^{-3}$ is W.

$X^{-2}$ and $X^{-1}$ may be any amino acid, and may be the same or different. Preferably, each is independently selected from the twenty (20) canonical amino acids and, more preferably, from S and T. However, one or both of $X^{-2}$ and $X^{-1}$ may be a non-canonical amino acid such as those mentioned above. Preferred non-canonical amino acids that may be present at positions −2 and −1 include derivatives of the twenty (20) canonical amino acids such as, for example, derivatives or analogues of serine (eg amino-oxyserine) and threonine (eg β-hydroxynorvaline (Hnv)).

In some preferred embodiments of the amino acid sequence of formula (I), $X^{-2}$ is S.

In some preferred embodiments of the amino acid sequence of formula (I), $X^{-1}$ is S.

In some preferred embodiments, a and b are both absent.

Where a is present, a may be selected from moieties such as an amino acid (eg any canonical or non-canonical amino acid), short amino acid sequences (eg 2 to 30, preferably 2 to 15, amino acids in length) or other chemical group. The additional moiety a may therefore be a functional moiety such as a biochemical tag or chelator such as Fluorescein isothiocyanate (5-FITC), 5-carboxyfluorecein (5-Fam), 5-(and-6)-Carboxytetramethylrhodamine] (5,6-TAMRA), an Alexa Fluor® dye (Life Technologies Corporation, Carlsbad, Calif., United States of America), a cyanine dye, near-IR dye, 1,4,7,10-tetraazacyclododecane-1,4,7,10-tetraacetic acid (DOTA), 2-(4,7-bis(2-(tert-butoxy)-2-oxoethyl)-1,4,7-triazonan-1-yl)acetic acid (NOTA), diethylene triamine pentaacetic acid (DPTA) etc, or a spacer/linker moiety to the N-terminal such as β-alanine, 8-amino-3,6-dioxaoctanoic acid ("mini-PEG™") and 11-amino-3,6,9-trioxaundecanoic acid ("mini-PEG3™") for attaching, for example, such a biochemical tag or chelator. In some preferred embodiments, a is an amino acid (in which case, a can be considered as $X^{-5}$, wherein $X^{-5}$ is any amino acid), and preferably selected from the group consisting of Ala, Gly, Ser and Thr. In some particularly preferred embodiments where a is present, a is Ser. Also, in some embodiments, a may comprise a cell-penetrating peptide (CPP) such as those mentioned above in paragraph [0023].

Where b is present, b may be selected from moieties such as an amino acid (eg any canonical or non-canonical amino acid), short amino acid sequences (eg of 2 to 5 amino acids in length) or other chemical group. The additional moiety b may therefore be a functional moiety such as a spacer/linker group to link the N-terminal extension (of formula (I)) to a ShK toxin polypeptide. In some embodiments, b is an amino acid selected from Ala and Gly.

Examples of the N-terminal extension suitable for inclusion in the ShK analogue include ESSS (SEQ ID NO: 1), EWSS (SEQ ID NO: 2), EESS (SEQ ID NO: 5), EWST (SEQ ID NO: 6), EWTT (SEQ ID NO: 7), EWTS (SEQ ID NO: 8) and SEWSS (SEQ ID NO: 9).

Notwithstanding the above, the ShK analogue of the present invention may additionally or alternatively, comprise amino acid sequences that have been modified either by natural processes, such as post-translational processing, or by chemical modification techniques such as those well known to those skilled in the art (eg Pegylation). Such modifications can occur anywhere in the analogue, including for example, within the peptide backbone, the amino acid side-chains and/or the C-terminal. It will also be appreciated that the same types of modifications may be present in the same or at varying degrees at several sites in the analogue. One preferred example of chemical modification is C-terminal amidation. Accordingly, the analogue of the present invention may preferably have an amide group at the C-terminal. Methods for the amidation of the C'-terminal of a peptide (eg α-amidation) are well known to those skilled in the art, including, for example, the methodologies described by Kim K-H et al. (Kim K-H et al., 2001). The C-terminal amide may avoid carboxypeptidase degradation of the analogue.

Preferably, the analogue is a polypeptide that shows the same pattern of disulphide bridging as the WT ShK polypeptide (ie Cys3-Cys35, Cys12-Cys28 and Cys17-Cys32) or otherwise has three disulphide bridges between cysteine residues at positions corresponding to 3/35, 12/28 and 17/32 of the amino acid sequence shown as SEQ ID NO: 4. As such, where the analogue is a polypeptide comprising a variant amino acid sequence of SEQ ID NO: 4 (ie an amino acid sequence that includes one or more minor variation(s) as described above), it is to be understood that, preferably, the analogue shows the same pattern of disulphide bridging as the WT ShK polypeptide (or otherwise has three disulphide bridges between cysteine residues at positions corresponding to 3/35, 12/28 and 17/32 of the amino acid sequence shown as SEQ ID NO: 4 notwithstanding the presence of variation(s) within the amino acid sequence). Moreover, such an analogue also preferably shows two short α-helices in substantially the same configuration as that of the WT ShK polypeptide.

Preferably, the analogue is a polypeptide consisting of the amino acid sequence:

```
                                              (SEQ ID NO: 10)
EWSSRSCIDTIPKSRCTAFQCKHSMKYRLSFCRKTCGTC.
```

Analogues comprising the N-terminal extension EWSS (SEQ ID NO: 2), including a Trp residue at position −3, provides some advantages as compared to the WT ShK polypeptide which lacks Trp. That is, the Trp residue can be substituted with a tryptophan derivative such as a fluorescent azatryptophan (for example, (4-Aza)Trp or (5-Aza)Trp (Lepthien S et al., 2008) or the recently developed (2,7-Aza) Trp (Shen J Y et al., 2013)), which can be incorporated into the polypeptide using recombinant techniques. An ShK analogue comprising an azatryptophan may be used, for example, as an optical probe for bioassays of polypeptide delivery or to investigate Kv1.3 channel distribution in neuronal or cancer tissues.

The analogue of the present invention may be produced using synthetic or recombinant techniques well known to those skilled in the art.

Preferably, the analogue is provided in an isolated form.

It is known to those skilled in the art that Kv1.3 channel blockers are potent inhibitors of the proliferation of T lymphocytes. It is also known that Kv1.3 channel blockers offer considerable promise for the treatment of autoimmune diseases mediated by $T_{EM}$ cells, such as rheumatoid arthritis (RA) and multiple sclerosis (MS), while avoiding possible cardiac- and neuro-toxicity. Moreover, it is recognised by those skilled in the art that an analogue showing Kv1.3 selectivity enables the targeting of disease-associated T cells and class-switched B cells without compromising other immune cells subsets; thereby avoiding generalised immunosuppression (which can lead to severe infections or malignancies). Accordingly, the analogue of the present invention may be suitable for the development of a therapeutic method for the treatment of autoimmune diseases and/or inhibiting T lymphocyte or class-switched B cell proliferation.

Thus, in a second aspect, the present invention provides a method of inhibiting T lymphocyte or class-switched B cell proliferation in a subject, said method comprising administering to the subject an effective amount of the analogue of the first aspect, optionally in combination with a pharmaceutically acceptable carrier.

Further, in a third aspect, the present invention provides a method of treating an autoimmune disease in a subject, said method comprising administering to the subject an effective amount of the analogue of the first aspect, optionally in combination with a pharmaceutically acceptable carrier.

The autoimmune disease to be treated in accordance with the method of the third aspect is preferably an autoimmune disease mediated by $T_{EM}$ cells. Examples of such diseases include RA, asthma, MS, T1DM and psoriasis. Other autoimmune diseases that may be treated in accordance with the method of the third aspect include ulcerative colitis (Koch Hansen L et al., 2014).

The subject to be treated will typically be a human. However, the invention is also applicable to non-human subjects such as, for example, livestock (eg cattle, sheep and horses), exotic animals (eg tigers, lions, elephants and the like) and companion animals (such as dogs and cats).

The analogue is preferably administered, adapted and/or formulated in a manner or medicament ensuring that, upon administration to the subject, an effective amount of said analogue is delivered to the subject. As such, the analogue may be, for example, formulated into any suitable medicament; such as a pharmaceutical composition for oral, buccal, nasal, subcutaneous, intramuscular, inhalative and intravenous administration. Typically, such a pharmaceutical composition will be administered to the subject in an amount which is effective to achieve a therapeutic effect, and may therefore provide between about 0.01 and about 100 µg/kg body weight per day of the analogue, and more preferably, provide from 0.05 and 25 µg/kg body weight per day of the analogue. A suitable pharmaceutical composition may be intended for single daily administration, multiple daily administration, or controlled or sustained release, as needed to achieve the most effective result. However, notwithstanding the above, it will be understood by those skilled in the art that the administered amount of the analogue, and the frequency of administration for any particular subject, may vary and depend upon a variety of factors including the activity of the analogue, the metabolic stability and length of action of the analogue, the age, body weight, sex, mode and time of administration, rate of excretion of the analogue, and the severity of the autoimmune disease to be treated. A suitable pharmaceutical composition may be formulated for inhalative administration (such as in the form of an aerosol), oral administration (such as in the form of a tablet, capsule, granules or powders), nasal administration (eg such as in the form of a spray or inhalable powder) or parenteral administration (such as by subcutaneous, intravenous or intramuscular injection or infusion).

In a fourth aspect, the present invention provides the use of the analogue of the first aspect in the treatment of an autoimmune disease, preferably an autoimmune disease mediated by $T_{EM}$ cells such RA and MS.

Moreover, in a fifth aspect, the present invention provides the use of the analogue of the first aspect in the preparation of a medicament for treating an autoimmune disease, preferably an autoimmune disease mediated by $T_{EM}$ cells such as RA and MS.

As mentioned above, the analogue of the present invention may be produced using recombinant techniques well known to those skilled in the art. Accordingly, in a further aspect of the present invention, the invention provides a polynucleotide molecule (preferably, in an isolated form) comprising a nucleotide sequence encoding the analogue of the first aspect and, preferably, one comprising or consisting of the amino acid sequence shown as SEQ ID NO: 10. In a still further aspect, the present invention provides a cloning or expression vector comprising such a polynucleotide molecule. Moreover, in yet a still further aspect, the present invention provides a host cell (eg a prokaryotic or eukaryotic cell) including the polynucleotide molecule or cloning or expression vector, wherein said host cell is capable, for example, of expressing the analogue in culture.

Notwithstanding the above, the analogue of the present invention may be suitable for the development of a therapeutic method for the treatment of diseases other than autoimmune diseases and other conditions, for example obesity (Tucker K et al., 2008; and Xu J et al., 2003), type-2 diabetes mellitus (T2DM) (Xu J et al., 2004), bone resorption in periodontal disease (Valverde P et al., 2005) and cancers (eg solid tumours, leukaemia and lymphomas)

(Leanza L et al., 2015). It is to be understood that such uses of the ShK analogues are included within the scope of the present invention.

As indicated above, for the treatment of cancers and other proliferative diseases or disorders, an ShK analogue of the present invention may be adapted for delivery to the cytoplasm of a cell where it may act to block Kv1.3 channels of the mitochondria (mitoKv1.3). This may be achieved by adding a cell-penetrating peptide (CPP) to the amino acid sequence of the ShK analogue (preferably at the C-terminal) or to the N-terminal extension (ie a of formula I may comprise a CPP). However, other approaches are also suitable including the use of coupled small molecule mimics of CPPs known as SMoCs (small molecule carriers; Okuyama M et al., 2007), the attachment of a CPP to the ShK analogue using "click chemistry" (eg using any of the methods described by Sharpless K B and R Manetsch, 2006, Kolb H C et al., 2001, and Tornoe C W et al., 2002), and the non-covalent attachment of a CPP to the ShK analogue (eg using the method described in Morris M C et al., 2001 involving the CPP known as Pep-1). Additionally or alternatively, the ShK analogue may be formulated for delivery to the cytoplasm of a cell; for example, the ShK analogue may be formulated as a liposomal preparation (especially a preparation comprising pH-sensitive liposomes for "endosomal escape"; Torchilin V P et al., 1993).

The present invention is hereinafter further described by way of the following non-limiting example and accompanying figures.

EXAMPLE 1

Design and Evaluation of a Sea Anemone Toxin ShK Analogues

Materials and Methods

Molecular modelling—Modelling of complexes of derivatives of ShK bound to Kv1.3 began with a model of ShK-192 bound to murine Kv1.3 (mKv1.3) that had been previously developed (Pennington M W et al., 2009). This model used the X-ray crystal structure of the $K^+$ channel from *Streptomyces lividans* (KcsA, PDBid 1BL8) as a template, to which was docked a model of ShK-192. Loop modelling of N-terminal extensions to ShK was performed using the MODELLER program (Eswar N et al., 2006). For each complex, 25 initial models were created, and for each of these models, 25 loop models (consisting of the N-terminal extension residues only) were considered; a total of 625 models were created for each N-terminal extension length.

MD simulations of the complexes of [ESSS]ShK, [EESS]ShK, [EISS]ShK, [ELSS]ShK, [EVSS]ShK and [EWSS]ShK with mKv1.3 were performed using the YASARA program (Yet Another Scientific Artificial Reality Application, www.yasara.org: YASARA Biosciences GmbH, Vienna, Austria); Ser-3 of [ESSS]ShK (in complex with the channel) was mutated to Glu, Ile, Leu, Val or Trp, respectively. The complex was embedded into a membrane consisting only of phosphtidyl-ethanolamine extending ~15 Å beyond the solute in the membrane plane, and with water extending ~10 Å beyond the solute perpendicular to the membrane. Boundary conditions were set to periodic. Residues were ionised according to their expected state at pH 7.4. Sodium and chloride ions replaced water molecules to effect a final ionic concentration of 0.9%. Further MD simulations were performed with [GEWSS]ShK and [SEWSS]ShK.

Standard AMBER03 force field parameters (Duan Y et al., 2003) were applied using a cut-off of 7.86 Å for all non-bonded interactions, while long-range Coulomb interactions were calculated using the Particle-Mesh-Ewald algorithm. No restraints were applied, which required the use of a short time-step of 1.25 fs for intramolecular forces and 2.5 fs for intermolecular forces. All simulations were performed at a temperature of 298 K and maintained at a total pressure of 1 bar. An initial restrained equilibration simulation lasting 250 ps was applied to permit lipid to pack around the solute without solvent interference. This was followed by 1.0 ns of unrestrained MD simulation.

Synthesis of N-terminally extended ShK analogues—[EESS]ShK and [ESSS]ShK were synthesised on a Prelude peptide synthesiser using a standard Fmoc-tBu strategy. The base polypeptide ShK was synthesised starting with Rink amide resin (Peptides International, Inc, Louisville, K.Y., United States of America). All couplings were mediated with diisopropyl carbodiimide and 6-chloro-hydroxybenzotriazole. Following completion of the synthesis of the 35-amino acid ShK sequence, the resin was divided into equal portions and the N-terminal extensions of ESSS (SEQ ID NO: 1) or EESS (SEQ ID NO: 5) were added to two separate aliquots. Following solid-phase assembly of the linear peptide chain, the polypeptide was cleaved from the solid support and simultaneously deprotected using Reagent K for 2 hours at room temperature (RT). The crude polypeptide was precipitated into ice-cold diethyl ether and washed thoroughly to remove cationic scavengers from the cleavage cocktail, dissolved in 50% aqueous acetic acid, diluted in water and then pH adjusted to 8.0 with $NH_4OH$.

Disulphide bond formation was facilitated with reduced and oxidised glutathione according to previously used protocols for ShK (Rauer H et al., 1999). The progress of folding was followed by RP-HPLC using a Phenomenex Luna C18 column (Phenomenex Inc., Torrance, Calif., United States of America) using a gradient of acetonitrile versus $H_2O$ containing 0.05% TFA from 10-70% over 35 min. Folding of the three disulphide bonds was also confirmed by the loss of 6 mass units from the crude material as determined by ESI-MS.

Expression and purification of [EWSS]ShK—[EWSS]ShK was expressed and purified as described previously (Chang S C et al., 2012). Briefly, [EWSS]ShK was expressed as a thioredoxin fusion protein that forms inclusion bodies in BL21(DE3) *E. coli* cells. These were solubilised and refolded in vitro, cleaved with enterokinase and purified to homogeneity by RP-HPLC followed by lyophilisation.

Electrophysiological analysis—Cells were studied using the whole-cell configuration of a standard patch-clamp technique at RT. The bath solution contained (in mM): 160 NaCl, 4.5 KCl, 2 $CaCl_2$, 1 $MgCl_2$, 10 HEPES, pH 7.2, 300 mOsm. Patch pipettes were filled with a solution containing (in mM): 145 KF, 10 HEPES, 10 EGTA, and 2 $MgCl_2$, pH 7.2, 290 mOsm, and had a resistance of 2-4 MΩ. Kv currents were elicited by repeated 200 ms depolarising pulses from a holding potential of −80 mV to 40 mV, applied every 30 seconds. The Port-a-Patch patch clamp system (Nanion Technologies GmbH, Munich, Germany) and NPC-1 chips with 2-3.5 MΩ resistance were also utilised in conjunction. $IC_{50}$ values of Kv blockers were calculated by fitting the Hill equation to the reduction of peak current measured at 40 mV.

Results

Modelling of N-terminal extensions to ShK—In a model of ShK-192 bound to Kv1.3, the N-terminal negatively-charged phosphono group was predicted to form a salt bridge with the side-chain ammonium group of Lys411 of the Kv1.3 channel. While the phosphono group presumably contributed to the high affinity of this analogue for the channel, it also represented a potential immunogenicity liability, and required chemical synthesis for its production and attachment to the peptide; it was hypothesised that these issues could be overcome by using canonical amino acids in place of the phosphono group. In the homology model of Kv1.3 in complex with ShK-192 (FIG. 1A), it was found that the phosphono group lay ~8 Å from the WT ShK toxin N-terminal, which is almost twice the distance between the N-terminal and the carboxylate of a fully-extended Glu residue (~4.7 Å). It was therefore considered likely that more than a single amino acid would be required to replace the phosphono group and its linker in order to span the required distance and maintain affinity for the channel.

Homology models of ShK-192 analogues with the phosphono group and linker replaced with an N-terminal Glu with 0, 1, or 2 intervening Ser residues were therefore created using the MODELLER program; the Ser amino acid was chosen to assist in maintaining the solubility and approximately mimic the properties of the mini-PEG spacer in ShK-192. Models with a Glu appended directly to the WT ShK toxin N-terminal could be generated such that the carboxylate of the Glu-1 could form a salt bridge with the side chain ammonium of Lys411 of the channel. However, these models could not be energetically differentiated from other models in which the salt bridge was absent (FIG. 1B). Similarly, with one or two intervening Ser residues, models could be generated with the necessary salt bridge, but once again these models were not significantly lower in energy than models in which the salt bridge was absent. With three intervening Ser amino acids, yielding an ESSS (SEQ ID NO: 1) extension, low energy models with the required interaction between the N-terminal Glu carboxylate and the ammonium of Lys411 of the channel could be obtained. In the lowest-energy model of [ESSS]ShK (FIG. 1C), apart from the salt bridge between Glu-4 and Lys411 of Kv1.3, the only other interaction of the extension with the channel is the side chain of Ser-3 with Pro377; the other Ser extension residues (at positions −1 and −2) project outwardly to the solvent.

Structure-activity relationship and modelling of [EWSS]ShK—The design of a Kv1.3-selective ShK analogue exploited the amino acid sequence variation between the Kv1.3 and Kv1.1 channels (FIG. 2). The two channels are highly homologous and present only seven surface-exposed residues that differ between them, with most of these differences being between residues of similar type; for example, Asp375 in Kv1.3 to Glu375 in Kv1.1 (D375E). The other differences are D376E, P377A, S378E, G380H, N382S and H404Y (FIG. 1A); of these, the first four residues lie in a turret between the S5 and pore helices, while H404 lies in a loop connecting the pore and S6 helices. Moreover, mouse and human Kv1.3 are very similar, with the only differences in surface-exposed residues between mouse and human being S378T and N382S; the sequences of mouse and human Kv1.1 are identical across the transmembrane and selectivity filter regions.

Of the seven surface residue differences between Kv1.3 and Kv1.1, only Pro377 of Kv1.3 contacts Ser-3 of the N-terminal extension of [ESSS]ShK in the model of the complex. The hydrophobic side chains of Ile, Leu and Val substituted at this position were all predicted to interact favourably with the side chain of this Pro residue (Liwo A et al., 1997), although the binding affinity with Pro relative to Ala (the residue in Kv1.1 corresponding to Pro377 in Kv1.3) is likely to be context-dependent (ie dependent upon whether the side-chains are solvent exposed or buried in the interior of the protein). The side chain of a Trp substituted at position −3 was, however, predicted to bind more tightly with the side chain of Pro than Ala independent of its environment. Importantly, Trp was predicted to best discriminate between Pro and Ala (ie exhibits the largest binding energy difference of all of the 20 canonical protein amino acids), and should thus best discriminate between Kv1.3 and Kv1.1.

Based on these observations, Ser-3 of the [ESSS]ShK analogue was substituted with Trp and the resulting model subjected to MD simulation. The final model after 1.0 ns of MD is presented in FIG. 1D. The side-chain of Trp-3 of the [EWSS]ShK analogue was predicted to interact with that of Pro377 of the Kv1.3 channel whilst at the same time maintaining the interaction of the Glu-4 carboxylate with Lys411. The side-chain hydroxyl of Ser-1 of this analogue was also predicted to form a hydrogen bond with the carboxylate of Asp433 of an adjacent channel monomer (a residue conserved between Kv1.3 and Kv1.1), further stabilising the complex.

MD simulations of the ShK derivatives [ESSS]ShK, [EISS]ShK, [ELSS]ShK and [EVSS]ShK, indicated that the side-chains of Ser-3, Ile-3, Leu-3 and Val-3, respectively, did not form stable interactions with the alkane side-chain of Pro377 (ie the loop containing Pro377 moved away from the extension during the simulation), suggesting that a larger side-chain group (such as the indole group in Trp) is necessary to span the distance. However, the salt bridge between the carboxylate of Glu-4 and Lys411 of Kv1.3 was maintained with all of the simulations.

Further MD simulations of the [EESS]ShK analogue, in which Ser-3 was replaced with Glu, in complex with Kv1.3 resulted in the Glu-3 also disengaging from its initial association with Pro377, although, again, the salt bridge between the carboxylate of Glu-4 of the analogue and Lys411 of Kv1.3 could be maintained with the alkane face of the side chain of Glu-3 packing against the alkane side chains of the invariant channel residues Val406 and Thr407.

In the MD simulations of the [GEWSS]ShK analogue, it was found that the interaction between the carboxylate of Glu-4 and the ammonium of Lys411 was lost resulting in a concomitant loss of the interaction between Trp-3 and Pro377, whereas modelling of the docking of [SEWSS]ShK with Kv1.3 indicates that this analogue maintains the salt bridge between the carboxylate of Glu-4 and Lys411 of Kv1.3 and allows the Trp-3 residue to fit "snuggly" into the binding site of the Kv1.3 channel flanked by Pro377. Thus, ShK analogues comprising a pentapeptide N-terminal extension, and particularly the [SEWSS]Shk analogue, show considerable promise as effective Kv1.3 channel blockers.

Synthesis of [ESSS]ShK and [EESS]ShK—The polypeptides were assembled using standard Fmoc-tBu solid-phase peptide synthesis. The crude product was oxidised using glutathione-mediated oxidative folding conditions that have been used successfully for many other ShK analogues. The polypeptides folded rapidly, resulting in the typical pattern of a major earlier-eluting peak by RP-HPLC followed by later-eluting misfolded and side-product species. [ESSS]ShK and [EESS]ShK were purified to homogeneity by preparative RP-HPLC. Each polypeptide had the correct mass by ESI-MS (data not shown), demonstrating that the three disulphide bonds had been formed. The yield was ~16% of the theoretical yield based upon the amount of starting resin for each of the polypeptides.

Expression and purification of [EWSS]ShK—Solubilised His-tagged fusion protein was denatured and loaded onto an NTA column as described previously (Chang S C et al., 2012), and the bound protein was refolded by gradual removal of denaturant. The eluted fusion protein was then cleaved with enterokinase and purified to homogeneity by RP-HPLC. Analytical RP-HPLC showed that the purified ShK analogue was essentially homogenous. High-resolution electrospray ionisation time-of-flight mass spectrometry (ESI-TOF) analysis of [EWSS]ShK produced an average mass of 4544 Da; this value was identical to the theoretical mass of 4544 Da for the [EWSS]ShK analogue with all six cysteines engaged in the three native disulphide bonds (Pohl J et al., 1995). The yield of [EWSS]ShK was ~2 mg/L.

Figure 3:
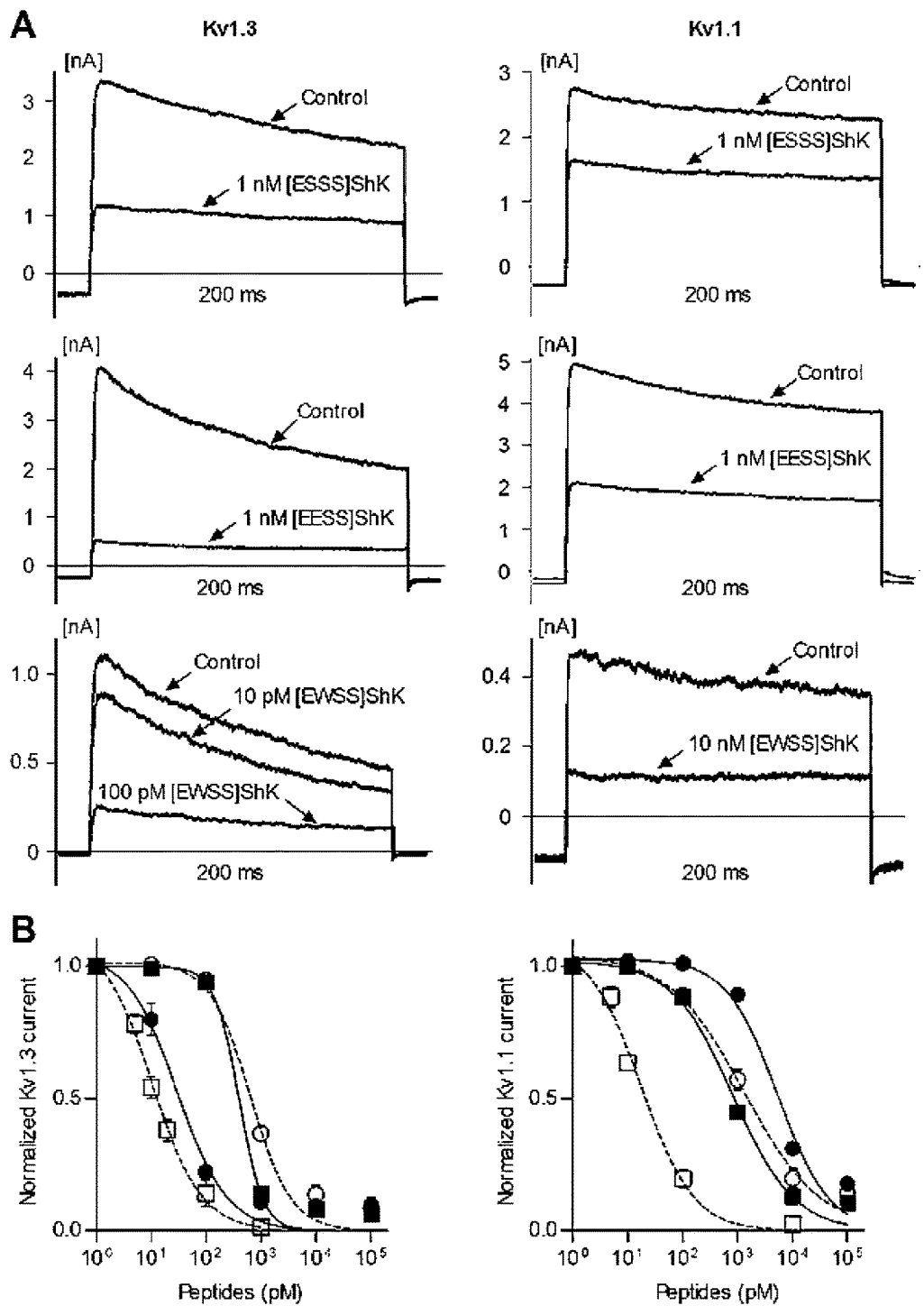
FIG. 3 provides graphical results showing the selectivity of N-terminally extended ShK analogues according to the present invention: (A) Effect of [ESSS]ShK (top), [EESS] ShK (middle) and [EWSS]ShK (bottom) on Kv1.3 and Kv1.1 channel currents; (B) Effects of [ESSS]ShK (○ dotted line), [EESS]ShK (■ solid line), [EWSS]ShK (● solid line) and ShK (□ dotted line) on Kv1.3 or Kv1.1 channel currents measured by whole-cell patch-clamp on L929 fibroblasts stably transfected with mKv1.3 or mKv1.1 (Grissmer S et al., 1994), respectively, and fitted to a Hill equation (N=3 cells per concentration). The panel on the left shows whole-cell Kv1.3 currents and the panel on the right shows whole-cell Kv1.1 currents. Data are presented as mean±s.e.m.

$K^+$ channel blocking activity—Well established whole-cell patch clamp electrophysiology assays were conducted to determine the potency and selectivity of the [ESSS]ShK, [EESS]ShK and [EWSS]ShK analogues on Kv1.3 an Kv1.1 channels (FIG. 3A). [ESSS]ShK inhibited Kv1.3 with an $IC_{50}$ of 657±79 pM, and showed lower affinity towards Kv1.1 with an $IC_{50}$ of 1327±386 pM, making it two-fold selective for Kv1.3 over Kv1.1. [EESS]ShK exhibited slightly higher affinity than [ESSS]ShK towards Kv1.3, with an $IC_{50}$ of 404±58 pM and an $IC_{50}$ of 830±116 pM for Kv1.1. [EESS]ShK was found to have 1.6-fold higher affinity for Kv1.3 than Kv1.1 as compared to [ESSS]ShK (Table 1, FIG. 3B), and was also two-fold selective for Kv1.3 over Kv1.1. Thus, both analogues have reduced affinity to $K^+$ channels and show a relatively low level of selectivity for Kv1.3 over Kv1.1. The implication is that neither Ser-3 nor Glu-3 was able to greatly discriminate between Pro377 in Kv1.3 and the corresponding Ala in Kv1.1. Recombinant [EWSS]ShK, however, exhibited high affinity for Kv1.3 with an $IC_{50}$ of 34±8 pM for mKv1.3, but significantly reduced affinity ($IC_{50}$=5371±912 pM) for the Kv1.1 channel (Table 1). Thus, the [EWSS]ShK analogue shows a similar level of selectivity for Kv1.3 as ShK-192, but with 4-fold higher affinity.

TABLE 1

Binding affinities ($IC_{50}$, pM) of ShK analogues

|  | Kv1.3 | Kv1.1 | Selectivity |
|---|---|---|---|
| ShK*[1] | 11 (2) | 18 (3) | 1.6 |
| ShK-186*[2] | 71 (4) | 6900 (500) | 97 |
| ShK-192*[2] | 140 (19) | 22000 (3000) | 157 |
| [ESSS]ShK | 657 (79) | 1327 (386) | 2.1 |
| [EESS]ShK | 404 (58) | 830 (116) | 2.1 |
| [EWSS]ShK | 34 (8) | 5371 (912) | 158 |

Numbers in parenthesis are standard errors of the mean.
*[1]Kalman K et al., 1998.
*[2]Pennington M W et al., 2009.

Discussion

Novel ShK analogues with N-terminal extensions consisting only of canonical amino acids were investigated. A number of these analogues showed selectivity for Kv1.3 channels over Kv1.1 channels, most notably an analogue with an EWSS (SEQ ID NO:2) tetrapeptide extension of the N-terminal. This [EWSS]ShK analogue showed only weak inhibition of Kv1.1 but maintained high potency against Kv1.3 channels ($IC_{50}$ 33±7 pM). Modelling studies suggested that the EWSS (SEQ ID NO: 2) tetrapeptide extension can mimic the interactions with Kv1.3 channels predicted for the phosphono moiety and hydrophilic linker in the analogue ShK-192. The tetrapeptide extension is also not susceptible to hydrolysis by phosphatases. The ShK analogues according to the present invention can be produced either using synthetic or recombinant techniques well known to those skilled in the art. They offer significant potential as the basis of therapeutic agents for the treatment of autoimmune diseases while avoiding generalised immunosuppression and possible cardiac- and neuro-toxicity through inhibition of off-target channels, particularly Kv1.1 channels.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

REFERENCES

Atkinson M A et al., *Lancet* 358:766 (2001).
Beeton C et al., *J Biol Chem* 278:9928-9937 (2003).
Beeton C et al., *Proc Natl Acad Sci USA* 103:17414-17419 (2006).
Beeton C et al., *Inflamm Allergy Drug Targets* 10:313-321 (2011).
Bennett J et al., *J Neuroimmunol* 229:180-191 (2010).
Berger T et al., *New Engl J Med* 349:139-145 (2003).
Chang S C et al., *Toxicon* 60:840-850 (2012).
Chi V et al., *Toxicon* 59:529-546 (2012).
Corcione A et al., *Proc Natl Acad Sci USA* 101:11064-11069 (2004).
Dorner T et al., *Curr Opin Rheumatol* 15:246-252 (2003).
Duan Y et al., *J Comput Chem* 24:1999-2012 (2003).
Eswar N et al., *Curr Protoc Bioinformatics* Chapter 5, Unit 5 6 (2006).
Fasth A et al., *Scand J Immunol* 60:199-208 (2004).
Fawell S et al., *Proc Natl Acad Sci USA* 91:664-668 (1994).
Friedrich M et al., *Arch Dermatol Res* 292:519-521 (2000).
Gilhar A et al., *J Invest Dermatol* 131:118-124 (2011).
Glasscock E et al., *J Neurosci* 30:5167-5175 (2010).
Grimmer S et al., *Mol Pharmacol* 45:1227-1234 (1994).
Gutman G A et al., *Pharmacol Rev* 57:473-508 (2005).
Hu L N et al., *Plos One* 8 (2013).
Kalman K et al., *J Biol Chem* 273:32697-32707 (1998).
Kim K-H et al., *Biotechnol Bioprocess Eng* 6:244-251 (2001).
Koch Hansen L et al., *J Crohns Colitis* 8(11):1378-91 (2014).
Kolb H C et al., *Agnew Chem Int Ed Engl* 40:2004-2021 (2001).
Koshy S et al., *J Biol Chem* 289:12623-12632 (2014).
Leanza L et al., *Leukemia* 27:1782-1785 (2013).
Leanza L et al., *Cell Calcium* 58:131-138 (2015).
Lepthien S et al., *Proc Natl Acad Sci USA* 105:16095-16100 (2008).
Lanigan M D et al., *Biochemistry* 41(40):11963-11971 (2002).
Liwo A et al., *J Comput Chem* 18:849-873 (1997).

Lovett-Racke A E et al., *J Clin Invest* 101:725-730 (1998).
Morris M C et al., *Nat Biotechnol* 19:1173-1176 (2001).
O'Connor K C et al., *J Clin Immunol* 21:81-92 (2001).
Okuyama M et al., *Nat Methods* 4(2):153-159 (2007).
Pennington M W et al., *Mol Pharmacol* 75:762-773 (2009).
Rauer H et al., *J Biol Chem* 274:21885-21892 (1999).
Ruben S et al., *J Virol* 63:1-8 (1989).
Sallusto F et al., *Annu Rev Immunol* 22:745-763 (2004).
Sharpless K B and R Manetsch, *Expert Opin Drug Discov* 7:489-501 (2012).
Shen J Y et al., *Nat Commun* 4:2611 (2013).
Tarcha E J et al., *J Pharmacol Exp Ther* 342:642-653 (2012).
Torchilin V P et al., *J Liposome Res* 3:201-255 (1993).
Tornoe C W et al., *J Org Chem* 67:3057-3064 (2002).
Tucker K et al., *Int J Obes (Lond)* 32(8):1222-1232 (2008).
Tudor J E et al., *Nat Struct Biol* 3:317-320 (1996).
Valverde P et al., *J Dent Res* 84(6):488-499 (2005).
Viglietta V et al., *J Clin Invest* 109:1511-1511 (2002).
Wagstaff K M and D A Jans, *Curr Med Chem* 13(12):1371-1387 (2006).
Wulff H et al., *J Clin Invest* 111:1703-1713 (2003).
Wulff H et al., *J Immunol* 173:776-786 (2004).
Xu J et al., *Hum Mol Genet* 12(5):551-559 (2003).
Xu J et al., *Proc Natl Acad Sci USA* 101(9):3112-3117 (2004).

---

The invention claimed is:

1. An analogue of *Stichodactyla helianthus* toxin ShK comprising an ShK toxin polypeptide and an N-terminal extension selected from the group consisting ESSS (SEQ ID NO: 1), EWSS (SEQ ID NO: 2), EESS (SEQ ID NO: 5), EWST (SEQ ID NO: 6), EWTT (SEQ ID NO: 7), EWTS (SEQ ID NO: 8) and SEWSS (SEQ ID NO: 9).

2. The analogue of claim 1, wherein the ShK toxin polypeptide comprises an amino acid sequence corresponding to:

RSCIDTIPKSRCTAFQCKHSMKYRLSFCRKTCGTC (SEQ ID NO: 4).

3. The analogue of claim 1, wherein the ShK toxin polypeptide comprises a variant amino acid sequence including a substitution of Met21.

4. The analogue of claim 1, wherein the N-terminal extension is EWSS (SEQ ID NO: 2).

5. The analogue of claim 1, wherein the analogue is a polypeptide with disulphide bridging between Cys3-Cys35, Cys12-Cys28 and Cys17-Cys32.

6. The analogue of claim 1, wherein the analogue is a polypeptide consisting of the amino acid sequence: EWSSRSCIDTIPKSRCTAFQCKHSMKYRLSFCRKTCGTC (SEQ ID NO: 10).

7. The analogue of claim 1, further comprising a cell-penetrating peptide.

8. The analogue of claim 1 in an isolated form.

9. The analogue of claim 1, wherein the analogue is a polypeptide with an amidated C-terminal.

10. A method of inhibiting T lymphocyte or class-switched B cell proliferation in a subject, said method comprising administering to the subject an effective amount of the analogue of claim 1, optionally in combination with a pharmaceutically acceptable carrier.

11. A method of treating an autoimmune disease in a subject, said method comprising administering to the subject an effective amount of the analogue of claim 1, optionally in combination with a pharmaceutically acceptable carrier.

12. The method of claim 11, wherein the autoimmune disease to be treated is an autoimmune disease mediated by $T_{EM}$ cells.

13. The method of claim 11, wherein the autoimmune disease to be treated is rheumatoid arthritis (RA) or multiple sclerosis (MS).

14. A method of treating a cancer in a subject, said method comprising administering to the subject an effective amount of the analogue of claim 1, optionally in combination with a pharmaceutically acceptable carrier.

15. The method of claim 14, wherein the cancer is a solid tumour, leukaemia or lymphoma.

* * * * *